United States Patent
Crane et al.

(10) Patent No.: US 8,746,031 B2
(45) Date of Patent: Jun. 10, 2014

(54) GLUCOSE SENSOR CALIBRATION

(75) Inventors: Barry Colin Crane, Oxfordshire (GB); William Paterson, Oxfordshire (GB)

(73) Assignee: Lightship Medical Limited, London (GB)

(*) Notice: Subject to any disclaimer, the term of this patent is extended or adjusted under 35 U.S.C. 154(b) by 211 days.

(21) Appl. No.: 13/297,975

(22) Filed: Nov. 16, 2011

(65) Prior Publication Data

US 2012/0096918 A1 Apr. 26, 2012

Related U.S. Application Data

(63) Continuation-in-part of application No. PCT/GB2010/000992, filed on May 17, 2010.

(60) Provisional application No. 61/213,208, filed on May 18, 2009.

(51) Int. Cl.
*A61B 5/1495* (2006.01)

(52) U.S. Cl.
USPC .......................................................... 73/1.03

(58) Field of Classification Search
None
See application file for complete search history.

(56) References Cited

U.S. PATENT DOCUMENTS

| | | | |
|---|---|---|---|
| 5,114,859 A | 5/1992 | Kagenow | 436/50 |
| 5,118,803 A | 6/1992 | Flatt et al. | 536/114 |
| 5,156,972 A | 10/1992 | Issachar | 435/288 |
| 5,188,803 A | 2/1993 | Hochberg | 422/99 |
| 5,992,211 A | 11/1999 | Skrtic | 73/1.03 |
| 6,037,178 A | 3/2000 | Leiner et al. | 436/50 |
| 6,387,672 B1 | 5/2002 | Arimori et al. | 435/183 |
| 7,785,535 B2 | 8/2010 | Chen et al. | 422/82 |
| 8,141,409 B2 * | 3/2012 | Crane et al. | 73/1.02 |
| 2003/0224523 A1 | 12/2003 | Thornberg et al. | 436/43 |
| 2006/0108218 A1 | 5/2006 | Gephart et al. | 204/400 |
| 2009/0018418 A1 | 1/2009 | Markle et al. | 600/317 |
| 2009/0018426 A1 | 1/2009 | Markle et al. | 600/365 |
| 2011/0152658 A1 * | 6/2011 | Peyser et al. | 600/365 |

FOREIGN PATENT DOCUMENTS

| | | |
|---|---|---|
| DE | 19546535 | 6/1997 |
| EP | 0560336 | 9/1993 |
| JP | 61-2070650 | 5/1985 |
| JP | 63-247646 | 4/1987 |
| WO | WO85/04719 | 10/1985 |
| WO | WO90/02938 | 3/1990 |
| WO | WO93/03362 | 2/1993 |
| WO | WO94/19683 | 9/1994 |
| WO | WO01/67079 | 9/2001 |
| WO | WO2008/001091 | 1/2008 |

OTHER PUBLICATIONS

International Search Report and Written Opinion for Appln No. PCT/GB2010/000992 dated Aug. 11, 2010, 17 pages.

* cited by examiner

*Primary Examiner* — Robert R Raevis
(74) *Attorney, Agent, or Firm* — Fish & Richardson P.C.

(57) ABSTRACT

A method of calibrating a glucose sensor, which method comprises:
  (a) preparing a first glucose-containing calibration solution by combining water or an aqueous solution with alpha and beta glucose, the alpha and beta glucose being provided in solid form;
  (b) exposing a glucose sensor to said first glucose-containing calibration solution and determining the sensor output;
  (c) exposing the glucose sensor to one or more further calibration solutions having different glucose concentrations from each other and from said first glucose-containing calibration solution and determining the sensor output for the or each calibration solution; and
  (d) determining a calibration curve from the sensor output data collected in steps (b) and (c).

18 Claims, 3 Drawing Sheets

GLUCOSE SENSOR CALIBRATION

RELATED APPLICATIONS

This application is continuation in part of International Application Number PCT/GB2010/000992, filed on May 17, 2010, which claims priority to U.S. Application No. 61/213,208, filed on May 18, 2009, the entire contents of which applications is hereby incorporated by reference.

FIELD OF THE INVENTION

The present invention relates to a method of calibrating a glucose sensor as well as calibration kits for use in this method and sensor kits which can be calibrated by this method.

BACKGROUND TO THE INVENTION

The use of glucose sensors in the medical field is widespread. The regular monitoring of blood glucose levels of diabetic patients at home as well as the use of glucose monitoring in intensive care units are two primary examples. The usual aim in developing a glucose sensor is to produce a digital electronic signal, which is proportional to the glucose concentration. The sensor usually comprises two main components, a chemical or biological part that reacts or complexes with the glucose (ideally specifically) to form new chemical or biological products or changes in energy that can be detected by means of the second component, a transducer. The chemical/biological component can be said to act as a receptor/indicator for glucose. A variety of transduction methods can be used including electrochemical (such as potentiometric, amperometric, conductimetric, impedimetric), optical, calorimetric and acoustic. After transduction the signal is usually converted to an electronic digital signal.

Since the signal generated by the chemical/biological reaction with the analyte is usually dependent not only on the concentration of the analyte but also on the characteristics of the sensor itself, such sensors usually require calibration before they can be utilised quantitatively. The way in which the signal varies with the analyte concentration determines the shape of the calibration curve (signal versus analyte concentration) and may define the number of calibration points. Typical calibration curves can be straight line, exponential, s-shaped etc and the principal of calibration applies to all methodologies of transduction for chemical or biological sensors.

Ideally, the sensor should be calibrated just before its use since some sensor characteristics that can affect the calibration curve vary with time (ageing effect). It is often the case that the time between sensor manufacture and use can be many months, so calibration at the point of manufacture can lead to inaccuracies in the end result. This means that the attendant clinician or nurse, or the home user, will be required to perform the calibration themselves. In order to maximise user compliance, the calibration process should be simple to perform, ideally invisible to the person performing the calibration, and be quickly completed.

Typical calibration techniques currently in use require the sensor to be inserted into three solutions having differing, but known, glucose concentrations (one of which may be zero), a reading to be taken for each solution, and a calibration curve to be generated. Since glucose has a tendency to degrade when sterilised in an aqueous solution, commonly the glucose solutions must be made up at the time of calibration by the addition of solid glucose to water or a solution such as saline. The entire calibration process is therefore both complicated and time consuming. Calibration of many currently available glucose sensors could 25 minutes or more to complete. There is therefore a need for a more rapid calibration technique for a glucose sensor, in order to improve user compliance.

SUMMARY OF THE INVENTION

The present inventors have found that the time needed for calibration of a glucose sensor can be reduced by preparing the calibration solutions in a particular manner. Specifically, the calibration solutions are prepared by the addition of both alpha and beta glucose to water or an aqueous solution.

As is well known, glucose exists in two predominant forms (isomers), termed the alpha and beta forms. In aqueous solution, the two forms will equilibrate by mutarotation of the glucose molecule. The resulting ratio of the two forms will be approximately 64:36 (beta:alpha). In the solid state, however, glucose is usually supplied in the alpha form. This means that when alpha glucose is added to water or an aqueous solution, it takes a period of time for the two forms to equilibrate (full equilibration can take a matter of hours).

Glucose sensors contain a receptor which has an affinity for glucose. Such receptors typically also have a greater affinity for either the alpha or beta form. This means that when calibration is carried out by the usual technique of addition of alpha glucose to water, the rate at which the sensor signal stabilises in the resulting solution is dependent on the rate of mutarotation.

The present inventors have shown that by the preparation of calibration solutions for a glucose sensor by adding both the alpha and beta forms to water or an aqueous solution, the rate of stabilisation of the sensor signal and hence the rate of calibration can be reduced.

The present invention accordingly provides a method of calibrating a glucose sensor, which method comprises:
  (a) preparing a first glucose-containing calibration solution by combining water or an aqueous solution with alpha and beta glucose, the alpha and beta glucose being provided in solid form;
  (b) exposing a glucose sensor to said first glucose-containing calibration solution and determining the sensor output;
  (c) exposing the glucose sensor to one or more further calibration solutions having different glucose concentrations from each other and from said first glucose-containing calibration solution (said different glucose concentration optionally being zero) and determining the sensor output for the or each calibration solution; and
  (d) determining a calibration curve from the sensor output data collected in steps (b) and (c).

Step (c) may be carried out either before or after steps (a) and/or (b).

Also provided is a calibration kit comprising
  a first compartment (1) containing water or an aqueous solution;
  a second compartment (2) containing glucose in solid form; and
  an optional third compartment (3) containing glucose in solid form, wherein at least one of the second and third compartments contains alpha glucose and at least one of the second and third compartments contains beta glucose, and wherein the first compartment is separated from the glucose-containing compartment(s) by a water impermeable dividing material.

Also provided is a glucose sensor kit comprising a glucose sensor and the calibration kit of the invention.

DETAILED DESCRIPTION OF THE INVENTION

Calibration Method

Figure 1:
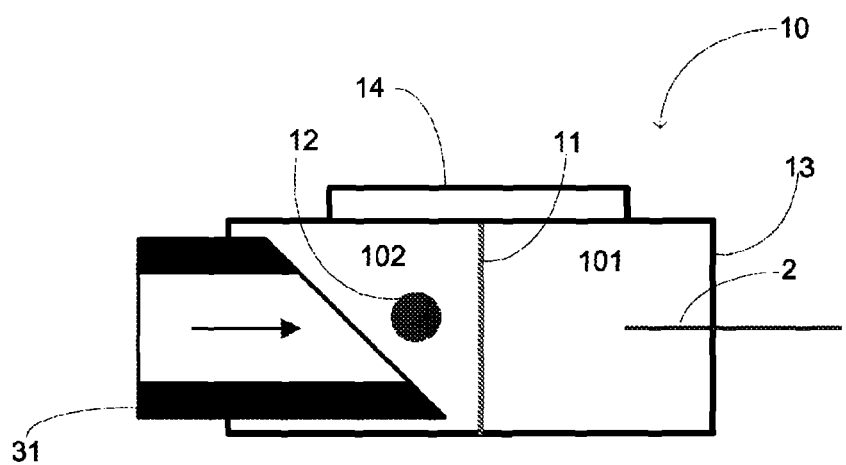
FIG. 1 depicts a calibration kit according to the invention for carrying out a two point calibration.

Calibration may be carried out as a two point calibration, using two data points to generate the calibration curve, but is more normally carried out using three or more data points. Of these data points, one is typically generated using a zero analyte concentration. The invention will largely be described with reference to a standard three point calibration using zero glucose concentration as one of the data points. However, it should be understood that the present invention can equally be used with two point calibration or four or more point calibration, and the use of a zero glucose concentration as one of the calibration points is not essential.

The method of the invention involves providing two or more, typically three, calibration solutions having differing glucose concentrations. Following any necessary preparation of each calibration solution, the sensor signal in the presence of the calibration solution is allowed to stabilize and a reading of the sensor output is taken. A suitable calibration algorithm is then used to generate a calibration curve. The skilled person would be familiar with the use of algorithms to generate a calibration curve in this manner.

Each calibration solution should have a different glucose concentration. The skilled person would be able to determine suitable concentrations of glucose for each solution. Typical concentrations should include zero and concentrations at the upper and lower end of those which are likely to be measured by the sensor. In the example of calibration of a glucose sensor for use with intensive care or diabetic patients, one calibration solution typically has a zero concentration, whilst the second and third calibration solutions typically have concentrations of, for example 5 mmolL$^{-1}$ and 10 mmolL$^{-1}$ respectively, or 5 mmolL$^{-1}$ and 15 mmolL$^{-1}$ respectively. Alternative concentrations could, however, be selected depending on the end use of the sensor. The volume of water or aqueous solution used, and the amount of glucose should be chosen according to the desired final concentrations of the calibration solutions.

At least one, and preferably at least two, more preferably all, of the glucose containing calibration solutions are prepared by mixing water or an aqueous solution with solid glucose, typically at the point of use. The water or aqueous solution may be pure water, saline or an isotonic solution. Isotonic solutions are preferred. The glucose comprises both alpha and beta glucose. Both forms of glucose are commercially available. For example, beta glucose is available from TCI Europe BV (product code G0047, CAS no. 28905-12-6) and can be produced in accordance with the methods described by Whistler and Buchanan (The Journal of Biological Chemistry 1938 "Preparation of *-glucose").

The alpha and beta glucose may be mixed prior to addition to the water or aqueous solution, or they may be added separately. If added separately, this addition may be simultaneous or at different times. Preferably, the alpha and beta glucose are mixed prior to addition to the water or aqueous solution, or are added at the same or substantially the same time. The glucose may be provided in the form of a powder or tablet or, if desired, a slow release capsule. Each tablet or capsule may contain both alpha and beta glucose, or separate tablets or capsules containing the alpha and beta glucose may be provided.

The proportion of alpha to beta glucose is preferably at or about the equilibrium level of 36% alpha to 64% beta, for example about 30 to 40% alpha and about 60 to 70% beta. However, the relative amounts of alpha and beta glucose can vary, for example from 10 to 90%, preferably 20 to 70% and more preferably 25 to 50% alpha; and from 10 to 90%, preferably 30 to 80% and more preferably 50 to 75% beta.

In one embodiment, the glucose may be provided as a freeze-dried solid. The freeze-dried solid may be prepared by freeze-drying an aqueous solution of glucose. Any appropriate freeze-drying technique may be used. The benefit of this embodiment is that the aqueous solution of glucose contains glucose at the equilibrium level. These levels are maintained in the freeze-dried solid, so that the freeze-dried solid contains to about 30 to 40% alpha glucose and about 60 to 70% beta glucose, for example 36% alpha and 64% beta. In this embodiment, the second and optionally third compartments of the calibration kit contain freeze-dried glucose. The calibration solutions are prepared by combining water or an aqueous solution with the freeze-dried glucose present in the second and/or third compartments.

Drying glucose solutions is known to result in elevated levels of alpha glucose. The present inventors have, however, surprisingly found that freeze-dried glucose maintains the same anomeric ratio which is present in aqueous solution. Accordingly, the use of freeze-dried glucose is a simple means to provide an equilibrium level mixture of alpha and beta glucose.

In one embodiment of the invention, the solution is mixed after addition of the glucose in order to increase the rate of dissolution. Mixing not only helps to speed up the calibration process, but also ensures that the entirety of the solid glucose is dissolved in the calibration solution. This is important in providing an accurate calibration.

A number of different mixing arrangements are provided, including mechanical means, magnetic or electromagnetic and ultra-sonication. For example, a moveable magnetic paddle may be provided within the first calibration compartment and an electromagnet provided around the compartment. Movement of the electromagnetic field generates movement of the paddle and causes mixing of the contents of the chamber. Alternatively, a mechanically operated paddle can be used. Particular embodiments of mixing means are further described in WO 2008/001091, the contents of which are incorporated herein by reference.

Following preparation of the calibration solution, the sensor is exposed to the solution and an output reading taken. In one embodiment, the sensor is in contact with the water or aqueous solution prior to addition of the glucose. In an alternative embodiment, the glucose is added in a first step and the sensor is subsequently exposed to the resulting solution. The use of a mixture of alpha and beta glucose ensures more rapid stabilization of the sensor output reading and enables the reading to be made more quickly.

The present invention enables calibration of a glucose sensor to be carried out very quickly. For example, a sensor output reading can typically be taken at a period of up to 5 minutes, preferably up to 2 minutes, 90 seconds or even up to 60 seconds after addition of the solid glucose to the water or aqueous solution. The entire calibration process may therefore be complete in up to 10 minutes, for example up to 5 minutes or even up to 2 minutes. These short times are achieved because the use of a mixture of alpha and beta glucose leads to an equilibrium being formed in the solution very quickly. Where the equilibrium proportions of alpha and beta glucose are used (36:64 alpha:beta), equilibrium is achieved as soon as the glucose is dissolved in the water or aqueous solution. Achieving a stable reading from the sensor is then dependent only on the response time of the sensor. The formation of an equilibrium in the solution is no longer necessarily a rate determining step in the calibration process.

In one embodiment of the invention, the various calibration solutions may be prepared separately, by addition of the relevant amount of glucose to separate volumes of water or aqueous solution. However, in a preferred embodiment, a single volume of water or aqueous solution is used to provide two or more, preferably at least three and most preferably all, of the calibration solutions. In this embodiment, typically a zero-glucose calibration solution is provided comprising water or an aqueous solution having substantially zero glucose concentration. An amount of solid glucose, comprising both alpha and beta glucose, is then added to this solution to provide a first glucose-containing calibration solution having a first glucose concentration. A further amount of glucose is then added to provide a second glucose-containing calibration solution having a second glucose concentration. In this embodiment, the method comprises at least the following steps:
- exposing the sensor to a zero-glucose calibration solution comprising water or an aqueous solution and containing no glucose and determining the sensor output;
- preparing a first glucose-containing calibration solution by combining said zero-glucose calibration solution with alpha and beta glucose, the alpha and beta glucose being provided in solid form;
- exposing the glucose sensor to said first glucose-containing calibration solution and determining the sensor output;
- preparing a second glucose-containing calibration solution by adding a further amount of alpha and beta glucose to said first glucose-containing calibration solution, the alpha and beta glucose being provided in solid form;
- determining the sensor output for the resulting second glucose-containing solution; and
- determining a calibration curve from the sensor output data obtained.

In one aspect of this embodiment, the steps of adding glucose to the solution are carried out with the sensor already in position within the solution. In this aspect, the sensor is immediately exposed to the resulting calibration solution as soon as addition has taken place. No action is therefore required on behalf of the user to expose the sensor to the solutions. This aspect assists in reducing the overall time taken to calibrate the sensor since the sensor output can be read as soon as the signal has stabilized.

Further details of particular methods of carrying out the method of the invention are discussed with regard to the particular embodiments below.

Calibration Kit

The invention also provides a calibration kit for use in the method of the invention. The calibration kit includes at least two compartments, the first containing the water or aqueous solution and the second and optional further compartments containing solid glucose. The kit is used by inserting the glucose sensor into the first compartment and, typically, determining the sensor output. The material dividing the first and second compartments is then broken to enable mixing of the glucose and the water or aqueous solution, thus providing a glucose-containing calibration solution having a chosen glucose concentration. Once mixing has taken place, the sensor output is again determined. This provides two calibration points, which can be used to generate a calibration curve.

In a typical embodiment, the alpha and beta glucose are provided together in the same compartment, usually the alpha and beta glucose are mixed. It is also envisaged, however, that the alpha and beta glucose are provided in separate compartments. In this case, the breakable material separating the first compartment from both the alpha glucose compartment and the beta glucose compartment are broken before the second sensor output reading is taken. Typically, both compartments are accessed at substantially the same time, to avoid any time delay in the equilibration of the resulting glucose solution. The further embodiments described herein refer to the alpha glucose and beta glucose being present in the same compartment.

The number of compartments present in the calibration kit will depend on (a) whether the alpha and beta glucose are provided in the same or different compartments, and (b) the number of calibration points to be used. In the preferred calibration kit in which the alpha and beta glucose are provided in the same compartment, a three point calibration will typically involve two separate glucose-containing compartments, each of which is separated from the first compartment by a water impermeable dividing material.

In order to provide improved storage stability, the solid glucose present in the calibration kit is typically stored in an inert gas atmosphere. This helps to avoid oxygen-induced degradation of the glucose.

The dividing material separating the glucose containing compartment(s) from the water containing compartment may be any material which can be broken, ruptured or removed causing the contents of the first and second compartments to mix. In one embodiment, the dividing material is an elastomeric material which is maintained under tension so that on piercing with a needle the material will be fully ruptured. Natural or synthetic rubbers are examples of such materials. In an alternative embodiment, the material is rigid, but is scored with fracture lines such that on piercing with a needle it readily fractures into components. Plastics and ceramics are examples of suitable rigid materials. Both of these types of dividing material provide a large opening between the first and second compartments, allowing quick mixing of the contents of the compartments. Alternative dividing materials include metal foils (e.g. aluminium foil) which may be coated with plastic.

The dividing material should be impermeable to water and glucose to avoid leakage between the two compartments of the calibration chamber. In one embodiment, one surface of the dividing material is metallised to assist in preventing water diffusion. The metallised surface is typically in contact with the second compartment which is preferably under an inert gas atmosphere.

The calibration kit of the invention will be described below with reference to a number of different embodiments, but the invention is not intended to be limited to these particular embodiments.

Embodiment 1

A first embodiment of a calibration kit according to the invention is depicted in FIG. 1. This calibration kit provides a two point calibration. The calibration kit 10 comprises two compartments 101 and 102, which are separated by a water-impermeable dividing material 11 e.g. a breakable dividing material. The first compartment 101 contains water or an aqueous solution. Typically, this compartment contains an isotonic solution and does not contain glucose. Thus, sensing of the glucose concentration in this compartment typically provides a zero reading.

The second compartment contains a source of glucose 12 in solid form. In this embodiment, the second compartment contains a mixture of alpha and beta forms of glucose. The second compartment may be under inert gas atmosphere (e.g. dry nitrogen) to avoid oxygen-induced irradiation degradation in the case that the calibration kit is sterilized by irradiation.

Calibration of a glucose sensor can be carried out by exposing the sensor to the first compartment 101 containing the water or aqueous solution. In the embodiment depicted in FIG. 1, the sensor is depicted within compartment 101. However, in alternative embodiments, the sensor may be provided separately. In this case, to enable the sensor to be inserted, outer wall 13 of the first compartment is typically at least in part piercable. For example, the outer wall 13 may be a septum which can be pierced by a needle. The sensor can be inserted into the first compartment through or within the needle. Once the sensing region is in place within the first compartment, a first reading of the sensor output is taken.

In an alternative aspect of this embodiment, a seal is provided between the sensor and the first compartment. Breaking the seal, e.g. by movement of the sensor or a part of the outer wall 13 of the first compartment, causes the content of the first compartment to flow around the sensor, thus exposing the sensor to the water or aqueous solution.

The dividing material separating first and second compartments is then broken or removed allowing the contents of these compartments to mix. In order to maintain sterility, the dividing material is typically broken or removed without opening the sealed calibration kit. Thus, the material is broken for example by movement of needle 31 in the direction of the arrow through the dividing material. This can be achieved, for example, by depression of a plunger attached to needle 31, either manually or by an automated process. The needle is here of substantially the same circumference as the second compartment, such that the analyte is pushed through the dividing material into the first compartment, aiding mixing.

In an alternative aspect of this embodiment, the sensor is inserted into the first compartment within a needle, and the needle, containing the sensor, can then be pushed forwards to rupture the dividing material.

Once the contents of the two compartments are mixed, a further calibration solution is provided having a greater concentration of glucose than the first calibration solution. The sensor output from a reading taken on this solution can be taken as soon as the sensor signal stabilises, thereby providing a second calibration point. The use of both alpha and beta glucose, rather than alpha glucose alone, provides more rapid stabilisation and therefore a reading of the sensor output can be made more quickly.

In an automated process, one or more of the steps of exposing the sensor to the first compartment and removing or breaking dividing material 11 may be machine-driven. A stepper motor or a stepper motor attached to a lead screw may be used in this regard.

Invasive sensors typically operate in a temperature range of 35-39° C. However, calibration is normally carried out at room temperature. Many sensors are sensitive to temperature variation, in which case a calibration curve generated at room temperature will be shifted to a different set of values at, say, 37° C. In one embodiment, therefore, a heating element (14 in FIG. 1) may be provided to increase the temperature within the calibration chamber to 37° C. prior to calibration.

A number of alternative embodiments of the invention are described below. Each of these embodiments is the same as the first embodiment, except as particularly described.

Embodiment 2

A preferred calibration will include three calibration points in order to provide a better fit in the calibration curve. To provide three calibration points, three separate calibration solutions having different concentrations of glucose are needed.

In one embodiment, a three point calibration is provided by including in the second compartment 102 a slow release capsule (not depicted) designed to release glucose into the water or aqueous solution only after the lapse of a period of time. The slow release capsule in this embodiment is provided in addition to the glucose source 12. On rupture/breakage/removal of the dividing material 11, the glucose source 12 will dissolve in the water or aqueous solution to allow a reading of the sensor to be taken for this first glucose-containing solution. The slow release capsule is designed such that its contents are released into the solution only after this reading, corresponding to the first glucose-containing solution, has been taken. Thus, a monitor detecting sensor output will observe a first increase in glucose concentration as the first glucose source dissolves, followed by a second distinct increase in glucose concentration following break-up of the slow release capsule.

In order to avoid long calibration times, capsules which dissolve in the range of from about 1 to 5 minutes are preferred. Polyethylene oxide capsules are examples of suitable materials. The precise release time of the capsule can be controlled by variation of the thickness of the capsule in a manner which is well known in the art.

Embodiment 3

Figure 2:
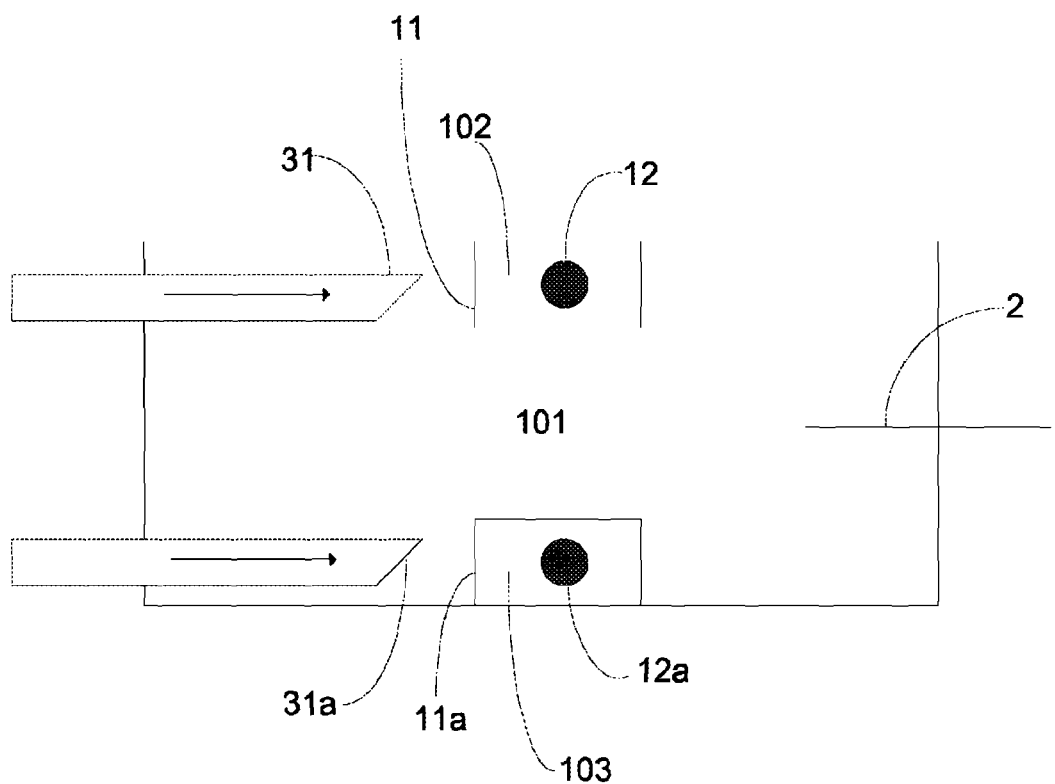
FIG. 2 depicts a calibration kit of the invention for carrying out a three point calibration.

An alternative embodiment of the calibration chamber is depicted in FIG. 2. In this embodiment, three compartments, 101, 102 and 103 are present. A dividing material 11, 11a separates each compartment. This embodiment provides a three point calibration by a different means. Following taking of the first reading of the water or aqueous solution in compartment 101, dividing material 11 of the second compartment 102 is pierced by needle 31. Mixing of the contents of compartments 101 and 102 provides a first glucose-containing calibration solution. A reading of the sensor output is taken once the sensor signal stabilises. The dividing material 11a of the third compartment 103 is then pierced by needle 31a. This causes glucose 12a to mix with the first glucose-containing calibration solution to provide a second glucose-containing calibration solution with a higher glucose concentration. The third reading of the sensor output can be taken once the sensor signal stabilises.

Sensor Kit

The present invention provides a sensor kit, which incorporates a glucose sensor and the calibration kit of the invention as described above. The sensor kit enables the sensor and calibration kit to be provided to the user in sterile form and in a very easy to use format. Further, the sensor kit enables the user to easily maintain sterility of the calibration kit and sensing region of the sensor during calibration.

The sensor typically has a sensing region, which is the part of the sensor which is contacted with the sample during analysis. In one embodiment, the sensing region of the sensor is located within the first compartment of the calibration kit. This means that the sensing region is in contact with the water or aqueous solution provided within that compartment. This may have advantages in terms of storage of the sensor, since some sensors are beneficially stored in solution rather than in dried form. Furthermore, on receipt of the sensor kit, the user can immediately take a reading of the sensor output for the solution in the first compartment and no further action is needed on behalf of the user to expose the sensor to the various solutions. The nature of the sensor for use with the present invention is not particularly limited. The sensor may be an invasive or implantable sensor, or it may be for in vitro measurement of glucose content. Sensors may be designed for measurement of the glucose content of physiological fluids such as blood or interstitial fluid, or for the measurement of glucose in other sample types.

In one embodiment, the sensor is an optical sensor comprising a glucose receptor, a fluorophore associated with the glucose receptor, a light emitter and a detector. A waveguide is typically provided, for example an optical fibre, to transmit the light to and from the emitter or detector. The fluorescence of the fluorophore is altered when glucose is bound to the receptor. Thus, the binding of glucose to the receptor generates a detectable signal that is responsive to the concentration of glucose. The signal detected may be, for example, the intensity of the emitted fluorescence, or the lifetime of the fluorescence.

Figure 3:
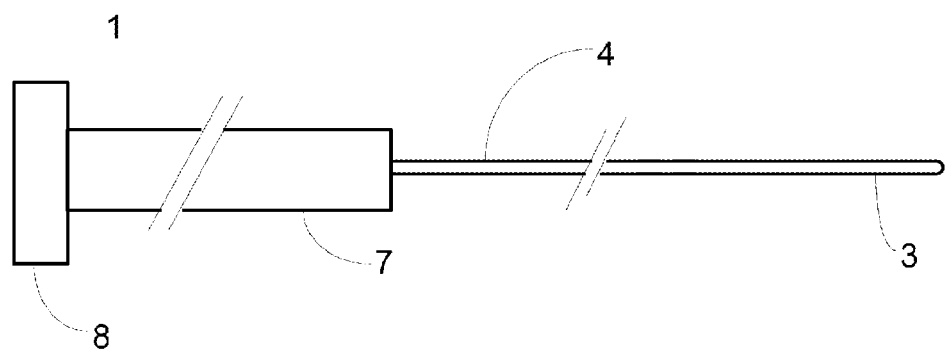
FIG. 3 depicts a glucose sensor for use with the invention.

An example of an optical fibre glucose sensor for use with the invention is depicted in FIG. 3. The sensor 1 comprises a tip 4 which may be adapted for insertion into a patient, for example insertion into a blood vessel through a cannular. The tip includes a sensing region 3 in which the glucose receptor and optionally a temperature sensor are positioned. The glucose receptor is immobilised on or in an optical fibre, such that a signal emitted by the receptor is transmitted through the optical fibre. The optical fibre extends through cable 7 to connector 8, which is adapted to mate with an appropriate monitor (not depicted). The monitor typically includes further optical cable that mates with the connector at one end and at the other bifurcates to connect to (a) an appropriate light source for the optical sensor and (b) a detector for the emitted signal. Electrical connection to any temperature sensor is also provided through connector 8 and appropriate detection equipment is provided by the monitor.

The sensing region of the sensor is typically coated with a membrane which should allow diffusion of glucose from the surrounding fluid to the receptor and, for in vivo use, should be haemocompatible.

The glucose receptor for such a fluorescent sensor may be any group or compound having an affinity for glucose. Boronic acid species are particularly envisaged for use as the glucose receptor. The skilled person in the art would be familiar with the use of boronic acid species and flurorophores in the optical detection of glucose. Examples of appropriate glucose receptor/fluorophore conjugates, however, are found in U.S. Pat. No. 6,387,672, the contents of which are incorporated herein by reference in their entirety.

The receptor and fluorophore are typically immobilised to the optical fibre in a hydrogel which allows diffusion of water and glucose to the receptor compound. Cross-linked polyacrylamide or polyhydroxyethylmethacrylate (p-HEMA) are examples of hydrogels that can be used.

Further examples of sensors which are suitable for use in the present invention are described, for example, in US 2009/0018418.

Figure 4:
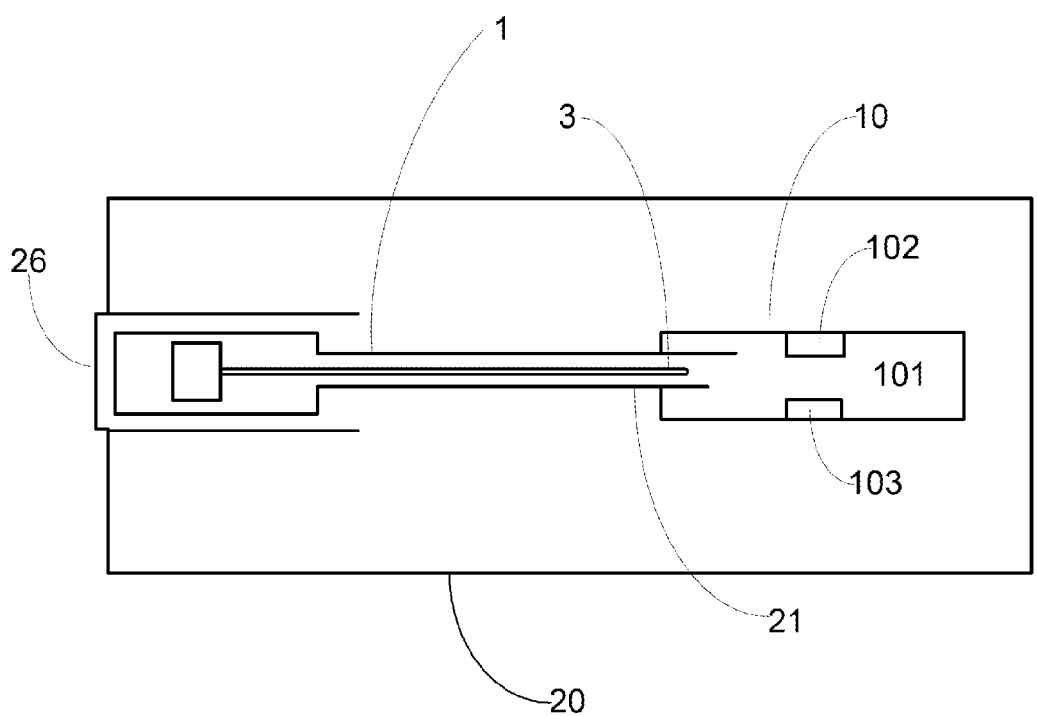
FIG. 4 depicts a sensor kit according to the invention.

An embodiment of the sensor kit of the invention is depicted in FIG. 4. The kit includes a container 20, which accommodates the sensor 1 and calibration kit 10. The calibration kit 10 is typically fixed into a locked position within the container. The sensor is contained within sensor housing 21 and is here depicted with the sensing region 3 of the sensor within the first compartment 101 of the calibration kit.

Means for breaking the dividing materials separating compartment 101 from compartments 102 and 103 are provided, for example needles 31 and 31a as depicted in FIG. 2. Such means typically extend outside housing 20 to enable user manipulation of these means without breaking the seal of the container and thus without loss of sterility.

The sensor housing containing the sensor is in one aspect movable laterally within the container, i.e. in a left/right direction as depicted in FIG. 4. A guide channel may be provided to ensure that movement of the sensor housing is restricted to this lateral direction and to limit free movement of the housing. In this way, the sensor can be moved within the sensor kit, for example a sensor provided outside the calibration kit 10 can be moved laterally so that it is within the calibration kit. In order to maintain sterility of the device, it is advantageous to be able to move the sensor and sensor housing without breaking the seal of the container. In the embodiment depicted in FIG. 4, this can be achieved by compressing compressible arm 26. This causes the sensor housing containing the sensor to move laterally within the container. The compressible arm may be configured in the shape of a compressible bellows.

The container 20 is typically sealed with a gas permeable lid (not depicted).

Further examples of particular features and embodiments of calibration kits and sensor kits which can be used with the method of the invention are described in WO 2008/001091 and US 2009/018426, the contents of which are incorporated herein in their entirety.

Example

An experiment was carried out to monitor the response of an optical glucose sensor to either alpha glucose, beta glucose or a mixture of alpha and beta glucose. The sensor's response to freeze-dried glucose was also monitored, in particular to determine if the response to the freeze-dried glucose was the same as the response to an alpha/beta mixture at a ratio of approximately 40:60 (alpha/beta).

In this example, an optical glucose sensor was used comprising an optical fibre having a glucose receptor and a fluorophore bound at its distal end. The glucose receptor was a diboronic acid and this receptor was associated with a fluorophore such that the binding of glucose to the receptor altered the emission pattern of the fluorophore. In this experiment, the intensity of fluorescence was monitored to provide an indication of glucose concentration.

Figure 5:
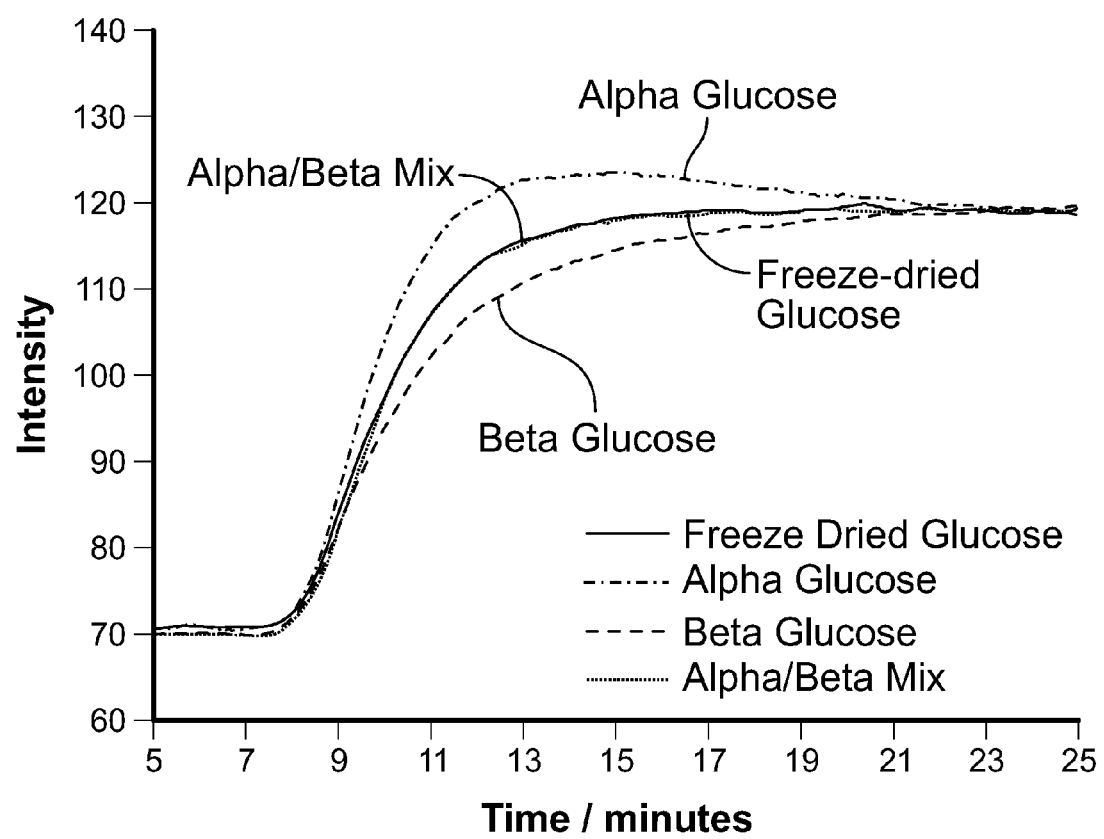
FIG. 5 shows that the response of an optical glucose sensor to solid samples of ∀-D-glucose, ∃-D-glucose, a 36:64 mix of ∀-D-glucose and ∃-D-glucose, and freeze-dried glucose.

The sensor was placed in a stirred solution of PBS at 37° C. When the sensor's fluorescent intensity was constant a sample of solid glucose was added. The solid glucose samples used were as follows:
1. Freeze-dried glucose prepared by freeze-drying an aqueous solution of D-glucose at equilibrium;
2. alpha-D glucose
3. beta-D glucose
4. a mixture of alpha-D-glucose and beta-D-glucose at a 36:64 ratio The response of the glucose sensor is depicted in FIG. 5. Diboronic acid receptors preferentially bind to alpha-D-glucose. Therefore, the results of FIG. 5 show that when solid alpha-D-glucose is added to the solution, an overshoot is seen until the anomeric ratio is equilibrated. The inverse is observed with beta-D-glucose. The response of the sensor to freeze-dried glucose is substantially identical to the response to the 40:60 mix of alpha-D-glucose and beta-D-glucose, indicating that the freeze-dried glucose retains the equilibrium anomeric ratio upon freeze-drying. In both cases, the response of the sensor reaches steady state more quickly than that of the alpha-D-glucose or beta-D-glucose alone. This experiment therefore demonstrates that the calibration time can be reduced by several minutes by the use of freeze-dried glucose or a mixture of alpha-D-glucose and beta-D-glucose.

The invention has been described with reference to various specific embodiments and examples. However, it is to be understood that the invention is in no way limited to these specific embodiments and examples.

The invention claimed is:

1. A method of calibrating a glucose sensor, which method comprises:
   (a) preparing a first glucose-containing calibration solution by combining water or an aqueous solution with alpha and beta glucose, the alpha and beta glucose being provided in solid form;
   (b) exposing a glucose sensor to said first glucose-containing calibration solution and determining the sensor output;
   (c) exposing the glucose sensor to one or more further calibration solutions having different glucose concentrations from each other and from said first glucose-containing calibration solution and determining the sensor output for the or each calibration solution; and
   (d) determining a calibration curve from the sensor output data collected in steps (b) and (c).

2. A method according to claim 1, wherein step (c) involves exposing the glucose sensor to two or more calibration solutions.

3. A method according to claim 1, further comprising preparing at least one of the one or more further calibration solutions used in step (c) by combining water or an aqueous solution with alpha and beta glucose, the alpha and beta glucose being provided in solid form.

4. A method according to claim 1, wherein the first glucose-containing calibration solution of step (a), and the or each glucose-containing calibration solution of step (c), is prepared using from 25% alpha glucose and 75% beta glucose to 50% alpha glucose and 50% beta glucose.

5. A method according to claim 4, wherein the first glucose-containing calibration solution of step (a), and the or each glucose-containing calibration solution of step (c), is prepared by combining water or an aqueous solution with freeze-dried glucose.

6. A method according to claim 1, wherein the determination of sensor output in step (b) is carried out within 2 minutes of combining the solid glucose and water or aqueous solution.

7. A method according to claim 1, wherein the method further comprises:
   exposing the sensor to a zero-glucose calibration solution comprising water or an aqueous solution and containing no glucose and determining the sensor output;
   and wherein
   the first glucose-containing calibration solution is prepared by combining said zero-glucose calibration solution with alpha and beta glucose, the alpha and beta glucose being provided in solid form; and
   the second glucose-containing calibration solution is prepared by adding a further amount of alpha and beta glucose to said first glucose-containing calibration solution, the alpha and beta glucose being provided in solid form.

8. A method according to claim 7 wherein the first glucose-containing solution is prepared by combining the zero-glucose calibration solution with freeze-dried glucose, and wherein the second glucose-containing calibration solution is prepared by adding a further amount of freeze-dried glucose to the first glucose-containing solution.

9. A calibration apparatus comprising
   a first compartment (1) containing water or an aqueous solution; and
   a second compartment (2) containing glucose in solid form,
wherein the second compartment contains alpha glucose and beta glucose, and wherein the first compartment is separated from the glucose-containing compartment(s) by a water impermeable dividing material.

10. A calibration apparatus according to claim 9, wherein the ratio of alpha glucose: beta glucose in the or each glucose-containing compartment is the same or different and is in the range 25:75 to 50:50.

11. A calibration apparatus according to claim 9 wherein the second compartment contains freeze-dried glucose.

12. A glucose sensor kit comprising a glucose sensor and a calibration apparatus according to claim 9.

13. A glucose sensor kit according to claim 12 wherein the second compartment of the calibration kit contains freeze-dried glucose.

14. A glucose sensor kit according to claim 12, wherein the glucose sensor comprises a sensing portion comprising a receptor for glucose, said sensing portion being located within the first compartment of the calibration kit.

15. A glucose sensor kit according to claim 12, wherein the glucose sensor comprises:
   a glucose receptor having an affinity for glucose;
   a fluorophore associated with said glucose receptor, the fluorescence of said fluorophore being altered in the presence of glucose;
   a light emitter; and
   a detector.

16. A calibration apparatus comprising
   a first compartment (1) containing water or an aqueous solution;
   a second compartment (2) containing glucose in solid form; and
   a third compartment (3) containing glucose in solid form,
wherein at least one of the second and third compartments contains alpha glucose and at least one of the second and third compartments contains beta glucose, and
wherein the first compartment is separated from the glucose-containing compartments by a water impermeable dividing material.

17. A calibration apparatus according to claim 16, wherein both the second and third compartments contain a mixture of alpha and beta glucose.

18. A calibration apparatus according to claim 16 wherein the second compartment and the third compartment contain freeze-dried glucose.

* * * * *